US010567660B2

(12) United States Patent
Elefteriu et al.

(10) Patent No.: US 10,567,660 B2
(45) Date of Patent: Feb. 18, 2020

(54) OVERLAY OF ANATOMICAL INFORMATION IN A MICROSCOPE IMAGE

(71) Applicant: Brainlab AG, Munich (DE)

(72) Inventors: Valentin Elefteriu, Kirchheim (DE); Theodor Mueller, Munich (DE)

(73) Assignee: Brainlab AG, Munich (DE)

( * ) Notice: Subject to any disclaimer, the term of this patent is extended or adjusted under 35 U.S.C. 154(b) by 204 days.

(21) Appl. No.: 15/116,594

(22) PCT Filed: Mar. 14, 2014

(86) PCT No.: PCT/EP2014/055133
§ 371 (c)(1),
(2) Date: Aug. 4, 2016

(87) PCT Pub. No.: WO2015/135590
PCT Pub. Date: Sep. 17, 2015

(65) Prior Publication Data
US 2016/0360117 A1    Dec. 8, 2016

(51) Int. Cl.
*H04N 5/232* (2006.01)
*A61B 34/00* (2016.01)
(Continued)

(52) U.S. Cl.
CPC ......... *H04N 5/23293* (2013.01); *A61B 34/20* (2016.02); *A61B 34/25* (2016.02);
(Continued)

(58) Field of Classification Search
None
See application file for complete search history.

(56) References Cited

U.S. PATENT DOCUMENTS

2006/0293557 A1* 12/2006 Chuanggui ............ A61B 90/36
                                                                  600/101
2008/0120577 A1*  5/2008 Ma ........................ G06F 3/017
                                                                  715/863
(Continued)

FOREIGN PATENT DOCUMENTS

GB            1431653            4/1976

OTHER PUBLICATIONS

International Search Report, PCT/EP2014/055133, dated Nov. 17, 2014, 3 pages.
(Continued)

*Primary Examiner* — Edemio Navas, Jr.
(74) *Attorney, Agent, or Firm* — Tucker Ellis LLP

(57) ABSTRACT

A medical data processing method of determining anatomical structure subset data describing a subset of a graphical representation 9 of an anatomical structure of a patient's body to be displayed simultaneously with a medical image of an anatomical body part 1, the method being constituted to be executed by a computer and comprising the following steps: a) acquiring predetermined anatomical structure representation data describing a graphical representation of the anatomical structure and its position in the patient's body; b) acquiring anatomical body part image data describing an image of an anatomical body part 1 of the patient imaged by an optical imaging apparatus 2 for display by a display apparatus 3; c) acquiring optical parameter data describing an optical parameter WD serving as a basis for displaying the anatomical body part image data; d) determining, based on the anatomical structure representation data and the anatomical body part image data and the optical parameter data, anatomical structure subset data describing a subset 9 of the anatomical structure representation data, which subset describes graphical representation of a structure subset of (Continued)

the anatomical structure to be displayed simultaneously with the image of the anatomical body part 1.

14 Claims, 2 Drawing Sheets

(51) Int. Cl.
    *A61B 34/20*     (2016.01)
    *A61B 90/20*     (2016.01)
    *H04N 5/265*     (2006.01)
    *A61B 90/00*     (2016.01)
    *A61B 90/25*     (2016.01)

(52) U.S. Cl.
    CPC .............. *A61B 90/20* (2016.02); *H04N 5/265* (2013.01); *A61B 90/25* (2016.02); *A61B 2034/2055* (2016.02); *A61B 2034/2057* (2016.02); *A61B 2090/365* (2016.02)

(56) References Cited

U.S. PATENT DOCUMENTS

2008/0292131 A1* 11/2008 Takemoto ............ H04N 13/246
    382/100
2011/0199532 A1   8/2011 Jin
2011/0316817 A1* 12/2011 Yamada ............. H04N 1/33376
    345/204

OTHER PUBLICATIONS

Janet Crossey, "A Rough Google Earth Guide", Article, Nov. 1, 2008, pp. 1-23, XP05496197, USA.

European Patent Office, Office Action for EP application No. 14711208.0, dated Aug. 6, 2018, pp. 1-6.

* cited by examiner

OVERLAY OF ANATOMICAL INFORMATION IN A MICROSCOPE IMAGE

RELATED APPLICATION DATA

This application is a national phase application of International Application No. PCT/EP2014/055133 filed Mar. 14, 2014 published in the English language.

The present invention relates to a medical data processing method of determining anatomical structure subset data describing a subset of a graphical representation of an anatomical structure of a patient's body which shall be displayed for example in an image received from a digital microscope. The invention also relates to a corresponding computer program and a computer executing that program.

For conducting medical procedures such as for example neurosurgery, it is often desirable to use a microscope in order to magnify the surgical situs for the operator. It is further desirable to supply the operator with information about the anatomical structures which he is currently viewing in the microscope image. Such information may for example define the position, geometry (in particular, at least one of shape and size), and physiological properties (such as the state of blood flow through a vessel) of an anatomical structure which is visible or not visible in the microscope image. Such information supports the operator in conducting the medical procedure.

A known approach for providing such information includes overlaying graphical information which has been extracted from pre-acquired medical images onto the microscope image. For example, graphical information representing a vessel tree may be overlaid onto a microscope image showing the operational situs in order to give the operator information about the position of relevant vessels. This may be supported for example by navigating the microscope relative to the operational situs, i.e. determining the position of the microscope relative to the situs by attaching a retroreflective marker device to the microscope and acquiring information about the position of the operational situs in a navigation reference system so as to track the position of the microscope relative to the situs with the navigation system. Based on the information about this relative position and information defining the position of anatomical structures represented in the pre-acquired medical image, the graphical information may be overlaid onto the microscope image so as to represent structures lying in the current field of view of the microscope.

In some cases, the graphical representation of anatomical structures segmented from the pre-acquired medical image information may have a size which renders part of the microscope image invisible when overlaid onto the microscope image. This problem is even increased in particular when a large microscope magnification is being used.

The following documents are of general relevance to the field of technology to which the present invention relates: GB 1 431 653 A, US 2011/0109532 A1.

A problem to be solved by the present invention therefore is to provide a method and apparatus which allow providing a microscope user with an improved overlay of graphical information onto the microscope image which in particular avoids undesirable obscuring of parts of the microscope image.

This problem is solved by the subject-matter of any appended independent claim. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can in particular be added to said other embodiment.

The present invention is designed to be used with a navigation application produced by Brainlab AG, which is known to be a reliable and precise software environment for conducting for conducting medical procedures and which is usable in connection with a head-up display.

EXEMPLARY SHORT DESCRIPTION OF THE PRESENT INVENTION

In the following, a short description of specific features of the present invention is given which shall not be understood to limit the invention only to the features or a combination of the features described in this section.

The present invention is directed to in particular a data processing method (which can be embodied by a computer program). The data processing method comprises steps of reading data defining a graphic representation of an anatomical structure (e.g. of a blood vessel) and overlaying the graphic representation onto a digital microscope image. Thereby, the user is provided with additional information about the anatomical situation in the neighbourhood of an anatomical body part which he is looking at through the microscope. The graphic representation is generated from e.g. a computed tomography which was produced before execution of the data processing method in accordance with the invention. The graphic representation is displayed in a manner such that, in dependence on an optical parameter of the digital microscope such as at least one of its current working distance and the selected magnification, only parts of the anatomical structure having a certain (predetermined) size are displayed as an image overlay.

The invention also relates to a computer running the corresponding computer program and a medical imaging device comprising that computer and the aforementioned digital microscope.

GENERAL DESCRIPTION OF THE PRESENT INVENTION

In this section, a description of the general, in particular preferred features of the invention is given.

In order to solve the aforementioned problem, a data processing method is provided. This data processing method is in particular a medical data processing method (i.e. a data processing method for use in a medical environment), of determining anatomical structure subset data describing (in particular defining, more particularly representing and/or being) a subset of an a graphical representation (e.g. an image or a graphical representation generated from an image) of an anatomical structure of a patient's body to be displayed simultaneously with a medical image of an anatomical body part.

Preferably, anatomical structure representation data is acquired which describes (in particular defines, more particularly represents and/or is) a graphical representation, for example the appearance (for example, the image appearance), of the anatomical structure and its position in the patient's body. The anatomical structure representation data is preferably predetermined, i.e. has been generated before the inventive method is executed (in particular, before the first step of the inventive method is executed). For example, the anatomical structure representation data has been generated from medical image data, in particular comprises (more particularly, consists of) medical image data. For example, it has been generated by applying a medical imaging modality to the patient's body (in particular, to the anatomical structure) and preferably segmenting the anatomical structure from the resulting medical image data. The medical imaging modality may be a computed tomography (in particular, a CT angiography) or magnetic resonance imaging (in particular, a magnetic resonance angiography). The anatomical structure may be any part of the patient's body and preferably comprises (in particular, consists of) at least one of vessels (for example blood vessels) and nerve fibres. Alternatively or additionally, the anatomical structure may be a hard tissue body part such as a bone or cartilage. In a specific embodiment of the invention, the anatomical structure is a vessel tree, for example a tree of blood vessels in the patient's brain.

The appearance of the anatomical structure is in particular defined by graphical features such as colours and contrasts in a graphical representation of the anatomical structure. This graphical representation may be embodied by image information or information determined from image information, such as an abstract representation of the anatomical structure segmented from medical image information showing the anatomical structure. For example, the appearance of the anatomical structure may be defined by a data set representing the three-dimensional structure of a tree of blood vessels, wherein for example vessels of different type (defined for example by the vessel being a vein or an artery, or by the vessel having a specific size, in particular diameter) may be identified by using uniquely assigned different colours for each type.

The anatomical structure representation data preferably also describes (in particular defines, more particularly represents and/or is) the position of the anatomical structure in the patient's body. In particular, the anatomical structure representation data comprises information defining the position of the anatomical structure in a reference system in which the envisaged medical procedure is planned and/or conducted. Such information may be associated with the anatomical structure representation data for example based on a position of the medical imaging apparatus relative to the anatomical structure, the position at the point of time of generating the medical image data being known.

Preferably, an anatomical body part image data is acquired which describes (in particular defines, more particularly represents and/or is) an image of an anatomical body part of the patient. The anatomical body part is preferably imaged by an optical imaging apparatus and the result of the imaging is described (in particular defined, more particularly represented by and/or contained in) the anatomical body part image data. For example, the image of the anatomical body part is a digital image and the anatomical body part image data comprises (in particular consists of) the data defining the digital image. The optical imaging apparatus therefore preferably is a digital imaging apparatus such as a digital camera and/or a digital microscope. The image of the anatomical body part is preferably displayed by a display apparatus, for example the display (such as an LCD display or a conventional computer monitor) which is operatively coupled to the optical imaging apparatus (in particular to a data processing unit such as an electronic circuit and/or a semiconductor-based microcontroller which executes the digital data processing within the functionality of the optical imaging apparatus). For example, the display is the display of the digital camera or a display rendering the image gathered by the digital microscope. This image is viewed in particular by the user wishing to have for example a magnified view of the anatomical body part.

The anatomical body part can be any anatomical body part of the patient and is preferably associated with the above-mentioned anatomical structure. In particular, the anatomical body part comprises the anatomical structure or is at least adjacent to the anatomical structure. For example, the anatomical structure may lie in front of or behind the anatomical body part in the imaging direction of the optical imaging apparatus. For example, the anatomical body part is a part of the patient's skin and the anatomical structure is a blood vessel lying below the surface (i.e. the uppermost layer) of the skin. The anatomical body part may also comprise (in particular, consist of) the anatomical structure.

Preferably, optical parameter data is acquired which describes (in particular defines, more particular represents and/or is) an optical parameter. The optical parameter is in particular an optical parameter of the optical imaging apparatus. Further particularly, the optical parameter is a control variable of the optical imaging apparatus which can be changed (in particular adjusted) for imaging the object to be imaged, e.g. the anatomical body part. For example, the optical imaging apparatus includes a lens having a variable focus. In particular, the optical imaging apparatus includes a focus lens including a zoom mechanism. The optical parameter then preferably at least one of the working distance of the optical imaging apparatus. The working distance is known to the skilled person to denote the distance between the object to be imaged (i.e. the anatomical body part) and the front end (when seen in the imaging direction) of the lens of the optical imaging apparatus. The in particular currently used working distance may be identical to the focal length, however the working distance may also be different from the focal length, in which case the image generally is not focussed.

Further particularly, the optical parameter is a specific focus position, in particular a real focal length, of the focus lens at which in particular the image of the anatomical body part is imaged by the optical imaging apparatus. The focal length is generally known to the skilled person as being the distance between the focus lens and the object to be imaged (in the present case, the anatomical body part) at which the optical imaging apparatus produces a sharp (i.e. focussed) image of the object to be imaged (i.e. the anatomical body part).

According to a further preferred embodiment, the optical parameter is a specific focus position, in particular a virtual (more particularly, an emulated) focal length, with which the image of the anatomical body part is to be displayed by the display apparatus. The emulated focal length can be for example a zoom factor applied for display the image of the anatomical body part on a display and/or monitor. The zoom factor defines in particular the level of magnification with which the image is displayed. The level of magnification can be defined for example as the amount (in particular number) of discrete image units such as pixels or voxels (in particular of the display device) onto which a predetermined amount of image information is distributed.

Preferably, the optical parameter data describes (in particular defines, more particularly represents and/or is) the value of the optical parameter. In particular, the optical parameter data contains a numeric value which the optical parameter attains during imaging of the anatomical body part and in particular during display of the anatomical body part image data by the display apparatus.

Preferably, anatomical structure subset data is determined based on the anatomical structure representation data and the anatomical body part image data and the optical parameter data. The anatomical structure subset data describes (in particular defines, more particularly represents and/or is) a subset of the anatomical structure representation data. The subset therefore is also called representation subset and describes (in particular defines, more particularly represents and/or is) a structure subset of the anatomical structure to be displayed simultaneously with the image of the anatomical body part.

The subset of the anatomical structure representation data preferably is a real subset of the anatomical structure representation data in the sense that it comprises less image information than the total image information contained in the anatomical structure representation data. However, the subset of anatomical structure representation data may—depending on in particular the current value of the optical parameter—also comprise the entire image information contained in the anatomical structure representation data. In particular, the structure subset of the anatomical structure is a real subset of the anatomical structure in the sense that the structure subset represents a part of the anatomical structure which is less than the total anatomical structure described by the anatomical structure representation data. However, the structure subset may also—depending in particular on the current value of the optical parameter—comprise the complete anatomical structure described by the anatomical structure representation data.

The subset of the anatomical structure representation data and therefore a graphical representation of the structure subset is preferably to be displayed (i.e. constituted for display) simultaneously with the image of the anatomical body part described by the anatomical body image data. Displaying the structure subset simultaneously with the image of the anatomical body part means in particular that the graphical representation of the structure subset is overlaid onto the image of the anatomical body part (i.e. the image of the anatomical body part is overlaid with the graphical representation of—in particular only—the structure subset, i.e. with the graphical information contained in the anatomical structure subset data).

The anatomical structure subset data is determined based on, in particular in dependence on, the optical parameter, in particular on the value of the optical parameter, described by the optical parameter data. For example, the size of the structure subset (and therefore also the subset of the anatomical structure representation data) is to be determined in dependence on the value of the optical parameter. Furthermore, the type of members of the structure subset is also determined in dependence on the value of the optical parameter. For example, the smaller the value of the optical parameter (for example the smaller the working distance), and therefore the larger the magnification of the anatomical body part in the image described by the anatomical body part image data, the smaller size parts of the anatomical structure are selected to be members of the structure subset. This means that smaller parts of the anatomical structure are selected to be members of the structure subset for a smaller working distance and/or larger magnification (in particular zoom factor) of the image information contained in the image of the anatomical body part). In consequence, only finer graphical representations for parts of the anatomical structure are displayed simultaneously with the image of the anatomical body part. Thus, overlaying these parts of the anatomical structure on a magnified image of the anatomical body part will decrease the risk that parts of the anatomical body part are obscured in the display. For example, only smaller vessels belonging to a vessel tree embodying the anatomical structure are displayed simultaneously with the image of the anatomical body part (for example with the image of brain tissue surrounding the respective vessel tree). The larger parts of the anatomical structure (i.e. parts of the anatomical structure having larger dimensions) are then selected for display only for a larger working distance or a smaller magnification (in particular smaller zoom factor), in particular they are then selected to be displayed in addition to the smaller parts of the anatomical structures.

However, it also within the framework of the invention that the e.g. the whole anatomical structure is divided into size classes, i.e. into classes into which its constituents are classified according to their size, and that for a specific value of the optical parameter, only members of one such classes or a number of such classes which is smaller than the total number of classes available are selected for display (in particular for overlay onto the image of the anatomical body part). For example, the graphical representation of the smaller size parts of the anatomical structure may be overlaid onto the microscope image only at a smaller working distance or a larger magnification and at a larger working distance or smaller magnification, the image of the anatomical body part is overlaid only with the graphical representation of the larger size parts of the anatomical structure may be selected.

Preferably, the optical imaging apparatus is navigated, i.e. its spatial relationship (in particular at least one of position and orientation) relative to the anatomical body part is tracked during acquisition of the anatomical body part image data. For example, a marker device is attached to the optical imaging apparatus (in particular in a known spatial relationship relative to the imaging unit such as the lens) and a surgical navigation system is used to determine the positions of the marker device (i.e. to track it) and thus the optical imaging apparatus. Further preferably, the position of the anatomical body part in a reference system in which the navigation (i.e. positional tracking) is conducted is known. For example, a marker device having a predetermined (i.e. known and preferably fixed) spatial relationship relative to the anatomical body part may be tracked by the surgical navigation system. On this basis, it may be determined which part of the appearance of the anatomical structure is associated with the image of the anatomical body part. Thus, the anatomical structure subset data can be reliably determined such that only a structure subset is displayed simultaneously with the image of the anatomical body part which is actually associated with the anatomical body part.

Preferably, combined display data is determined based on the anatomical structure subset data and the anatomical body part image data. The combined display data describes (in particular defines, more particularly represents and/or is) a combined data set comprising the image of the anatomical body part and a graphical representation (in particular, an image) generated from the subset of the anatomical structure image data. The combined data set describes (in particular defines, more particularly represents and/or is or includes) in particular an overlay of the image of the anatomical body part with the appearance of the subset of the anatomical structure. For example, the image of the anatomical body part may be overlaid with a graphical representation of part of a vessel tree embodying the anatomical structure. This part of the vessel tree embodies the subset of the anatomical structure and is in particular less than the complete vessel tree described by the anatomical structure representation data. The method preferably also comprises a step of displaying the information contained in the combined data set on the display apparatus. This allows the user such as a physician to view for example an overlay of the microscope image of the anatomical body part with the structure subset depending on the value of the optical parameter, thereby avoiding obscuring more of the image of the anatomical body part than necessary to gather an impression of the position of the members of the structure subset of the anatomical structure relative to the parts of the anatomical body part displayed using the current value of the optical parameter.

Preferably, the inventive method comprises a step of acquiring optical parameter interval data describing (in particular defining, more particularly representing and/or being) a predetermined interval of values for the optical parameter (i.e. values of the optical parameter, namely values which the optical parameter may attain) in which the anatomical structures subset data can be determined. The interval described by the optical parameter interval data therefore is in particular an interval of working distance values or focal length values in which it is sensible to determine the structure subset. This avoids spending unnecessary effort on trying to determine the anatomical structure subset data if the currently used for example working distance is outside an interval in which the working distance is expected to lie when the operator wants to view for example a microscope image of the anatomical body part. For example, the optical parameter interval data may define that the interval is less than 300 mm working distance.

Based on the optical parameter data and the optical parameter interval data, it is then preferably determined whether the value of the optical parameter described by the optical parameter data lies in the interval defined by the optical parameter interval data. The anatomical structure subset data is then preferably determined if (and only if) it is determined that the value of the optical parameter lies in the interval. Preferably, interval indication data is determined if it is determined that the value of the optical parameter lies in the interval. The interval indication data describes (in particular comprises, more particularly defines, for example represents and/or is) information to be output to the user that the optical parameter lies in the interval. In particular, the user is presented with information indicating whether the optical parameter lies in the predetermined interval. For example, the interval indication data describes (in particular defines, more particularly represents and/or is) visual and/or graphical information (e.g. coloured graphical information) may be output to the user in particular in the display of the display apparatus currently as a position in particular relative to the anatomical body part in which the optical parameter (for example the working distance) lies in the predetermined interval described by the optical parameter interval data. For example, a graphical pattern in green colour may be output on the display of the display apparatus in this case. If it is determined that the value of the optical parameter is not lying in the interval, a graphical pattern in red colour may be output to the user. The user is thus presented with visual information about the usefulness of the present position of the optical imaging apparatus in particular relative to the anatomical body part. Alternatively or additionally, the interval indication data describes (in particular defines, more particularly represents and/or is) audio-information which can be output via an audio indicating device, for example a loudspeaker, operatively coupled to the data processing unit of the optical imaging apparatus (e.g. a sound indicating that the current value of the optical parameter lies in the interval or does not lie in the interval).

Preferably, optical parameter variation data is determined based on the optical parameter interval data and the optical parameter data. The optical parameter variation data describes (in particular defines, more particularly represents and/or is) a direction in which the optical parameter has to be varied to allow determination of the anatomical structure subset data. The optical parameter variation data therefore indicates whether the value of the optical parameter has to be increased or decreased in order to reach a current value of the optical parameter lying in the predetermined interval. The interval indication data preferably comprises the optical parameter variation data, for example the interval indication data may comprise visual information for the user telling him how to move the optical imaging apparatus relative to the anatomical body part in order to vary the optical parameter in the direction indicated by the optical parameter variation data. For example, the visual information indicating the direction may be an arrow symbol displayed in the display of the display apparatus and indicating the moving direction. Alternatively or additionally, the interval indication data may comprise audio-information which can be output to the user and indicates to him the direction in which the optical parameter should be varied or the optical imaging apparatus should be moved. Instead of or in addition to moving the optical imaging apparatus relative to the anatomical body part, the respective value of the optical parameter may also be reached by varying the focal length of the focus lens of the optical imaging apparatus.

Preferably, the anatomical structure image data comprises class information describing (in particular defining, more particularly representing and/or being) classes which describe (in particular define, more particularly represent and/or are) structure subsets of the anatomical structure. In particular, each one of the structure subsets denotes (in particular defines) a part (or, more generally, parts) of the anatomical structure having a predetermined size. For example, the classes may define the maximum diameter of a vessel which is part of the vessel tree embodying the anatomical structure which it may have to be assigned to the respective class and therefore the respective structure subset. The classes may therefore overlap in one direction along the length scale, in particular all parts of the anatomical structure having a relatively smaller size may also be members of the structure subsets and therefore classes of which the parts of the anatomical structure having a relatively larger size are also members. The classes and therefore structure subsets may, according to a further embodiment, not overlap such that for a specific value of the optical parameter, only a part of the appearance of the anatomical structure (namely the appearance of the structure subset) is displayed simultaneously with the image of the anatomical body part). Thus, even if for example the working distance is chosen to be a maximum working distance (in particular the maximum working distance defined by the optical parameter interval data), not all parts of the anatomical structure (for example, not all vessels belonging to the vessel tree) are displayed simultaneously with (i.e. are overlaid onto) the image of the anatomical body part. For example, only the structure subset comprising the larger size parts of the anatomical structure (such as larger vessels in the vessel tree) may be displayed in this case. To this end, each structure subset is preferably associated with the predetermined value of the optical parameter and, depending on the value of the optical parameter described by the optical parameter data, the respective structure subset is determined (in particular selected) for simultaneous display with the image of the anatomical body part. Thus, the anatomical structure subset data is determined based on (in particular by) determining the structure subset which is associated with the actual value of the optical parameter. Preferably, the size of the part of the anatomical structure contained in a respective one of the classes becomes smaller, the smaller the value of the optical parameter associated with the respective class becomes. This is in particular the case if the optical parameter is the working distance. If the optical parameter is the magnification (for example, zoom factor), the size of the part of the anatomical structure contained in a respective one of the classes preferably becomes smaller the larger the associated value of the optical parameter becomes.

The invention also relates to a program which, when running on a computer, causes the computer to perform one or more or all of the method steps described herein.

Alternatively or additionally, the invention also relates to a program storage medium on which the program is stored (in particular in a non-transitory form). Alternatively or additionally, the invention also relates to a computer comprising said program storage medium. Alternatively or additionally, the invention also relates to a (physical, in particular electrical, in particular technically generated) signal wave, in particular a digital signal wave, carrying information which represents the program, in particular the aforementioned program, which in particular comprises code means which are adapted to perform any or all of the method steps described herein.

The invention also relates to a medical imaging device, comprising the following features:
 a) an optical imaging apparatus such as the above-mentioned digital camera or digital microscope;
 b) a display apparatus operatively coupled to the optical imaging apparatus; the display apparatus is in particular the display of the digital camera or a display coupled to the digital microscope to render an image captured by the digital camera or digital microscope, respectively;
 c) the aforementioned computer, the computer being operatively coupled to the optical imaging apparatus and the display apparatus to conduct the data processing as described above.

In particular, the invention does not involve or in particular comprise or encompass an invasive step which would represent a substantial physical interference with the body requiring professional medical expertise to be carried out and entailing a substantial health risk even when carried out with the required professional care and expertise. In particular, the invention does not comprise a step of positioning a medical implant in order to fasten it to an anatomical structure or a step of fastening the medical implant to the anatomical structure or a step of preparing the anatomical structure for being fastened to the medical implant. More particularly, the invention does not involve or in particular comprise or encompass any surgical or therapeutic activity. The invention is instead directed in particular to positioning the tool relative to the medical implant, which may be outside the patient's body. For this reason alone, no surgical or therapeutic activity and in particular no surgical or therapeutic step is necessitated or implied by carrying out the invention.

It is within the scope of the present invention to combine one or more features of one or more embodiments in order to form a new embodiment wherever this is technically expedient and/or feasible. Specifically, a feature of one embodiment which has the same or a similar function to another feature of another embodiment can be exchanged with said other feature, and a feature of one embodiment which adds an additional function to another embodiment can in particular be added to said other embodiment.

Definitions

In this section, definitions for specific terminology used in this disclosure are offered which also form part of the present disclosure.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit or CPU) which executes the computer program elements, and optionally a volatile memory (in particular a random access memory or RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which in particular comprises technical, in particular tangible components, in particular mechanical and/or electronic components. Any device mentioned as such in this document is a technical and in particular tangible device.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (so-called medical imaging modalities and/or radiological imaging methods) such as for instance computed tomography (CT) and cone beam computed tomography (CBCT, in particular volumetric CBCT), x-ray tomography, magnetic resonance tomography (MRT or MRI), conventional x-ray, sonography and/or ultrasound examinations, and positron emission tomography. The image data thus generated is also termed "medical imaging data". Analytical devices in particular are used to generate the image data in apparatus-based imaging methods. The imaging methods are in particular used for medical diagnostics, to analyse the anatomical body in order to generate images which are described by the image data. The imaging methods are also in particular used to detect pathological changes in the human body.

The method in accordance with the invention is in particular a data processing method. The data processing method is preferably performed using technical means, in particular a computer. The data processing method is preferably constituted to be executed by or on a computer and in particular is executed by or on the computer. In particular, all the steps or merely some of the steps (i.e. less than the total number of steps) of the method in accordance with the invention can be executed by a computer. The computer in particular comprises a processor and a memory in order to process the data, in particular electronically and/or optically. The calculating steps described are in particular performed by a computer. Determining steps or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term "computer" includes a cloud computer, in particular a cloud server. The term "cloud computer" includes a cloud computer system which in particular comprises a system of at least one cloud computer and in particular a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. In particular, the term "cloud" is used in this respect as a metaphor for the Internet (world wide web). In particular, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer in particular comprises interfaces in order to receive or output data and/or perform an analogue-to-digital conversion. The data are in particular data which represent physical properties and/or which are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals in particular represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer.

The expression "acquiring data" in particular encompasses (within the framework of a data processing method) the scenario in which the data are determined by the data processing method or program. Determining data in particular encompasses measuring physical quantities and transforming the measured values into data, in particular digital data, and/or computing the data by means of a computer and in particular within the framework of the method in accordance with the invention. The meaning of "acquiring data" also in particular encompasses the scenario in which the data are received or retrieved by the data processing method or program, for example from another program, a previous method step or a data storage medium, in particular for further processing by the data processing method or program. The expression "acquiring data" can therefore also for example mean waiting to receive data and/or receiving the data. The received data can for example be inputted via an interface. The expression "acquiring data" can also mean that the data processing method or program performs steps in order to (actively) receive or retrieve the data from a data source, for instance a data storage medium (such as for example a ROM, RAM, database, hard drive, etc.), or via the interface (for instance, from another computer or a network). The data can be made "ready for use" by performing an additional step before the acquiring step. In accordance with this additional step, the data are generated in order to be acquired. The data are in particular detected or captured (for example by an analytical device). Alternatively or additionally, the data are inputted in accordance with the additional step, for instance via interfaces. The data generated can in particular be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, in particular determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is in particular part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is in particular known to a navigation system and is for example stored in a computer of the navigation system.

A "reference star" refers to a device with a number of markers, advantageously three markers, attached to it, wherein the markers are (in particular detachably) attached to the reference star such that they are stationary, thus providing a known (and advantageously fixed) position of the markers relative to each other. The position of the markers relative to each other can be individually different for each reference star used within the framework of a surgical navigation method, in order to enable a surgical navigation system to identify the corresponding reference star on the basis of the position of its markers relative to each other. It is therefore also then possible for the objects (for example, instruments and/or parts of a body) to which the reference star is attached to be identified and/or differentiated accordingly. In a surgical navigation method, the reference star serves to attach a plurality of markers to an object (for example, a bone or a medical instrument) in order to be able to detect the position of the object (i.e. its spatial location and/or alignment). Such a reference star in particular features a way of being attached to the object (for example, a clamp and/or a thread) and/or a holding element which ensures a distance between the markers and the object (in particular in order to assist the visibility of the markers to a marker detection device) and/or marker holders which are mechanically connected to the holding element and which the markers can be attached to.

A navigation system, in particular a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) in particular comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

DESCRIPTION OF THE FIGURES

In the following, the invention is described with reference to the enclosed figures which represent a preferred embodiment of the invention. The scope of the invention is however not limited to the specific features disclosed in and described with reference to the figures.

FIG. 1 shows a setup for imaging an optical body part represented by the outer surface of the patient's skin on the skull 1 with an optical imaging apparatus represented by digital microscope 2. The digital microscope 2 is supported on a movable arm 7 which is operatively coupled to a driving unit embodied by an electric motor. The electric motor receives control signals from a computer 5 for controlling the movement of the arm 7 and therefore the position of digital microscope 2. The digital microscope 2 acquires and displays the anatomical body part image data on a displays disposed in the digital microscope 2. The computer 5 is operatively coupled to a display apparatus embodied by a monitor 3 for displaying visual information to the user (for example the interval indication data and/or the optical parameter variation data. Furthermore, the computer 5 serves as the computer of a navigation system and is operatively coupled via data link 6 to a stereoscopic camera 4 which tracks the position of the digital microscope 2 by detecting reference star 8 which is fastened to the housing of the digital microscope 2 in a known and fixed spatial relationship. The position of the skull 1 is known to the computer 5. The working distance is abbreviated in the Figures as WD. The digital microscope 2 is positioned at a working distance of 250 mm from the surface of the patient's skull 1. The working distance is an example for the optical parameter. The information about the value of the working distance is contained in the optical parameter data and acquired by the computer 5.

Figure 1:
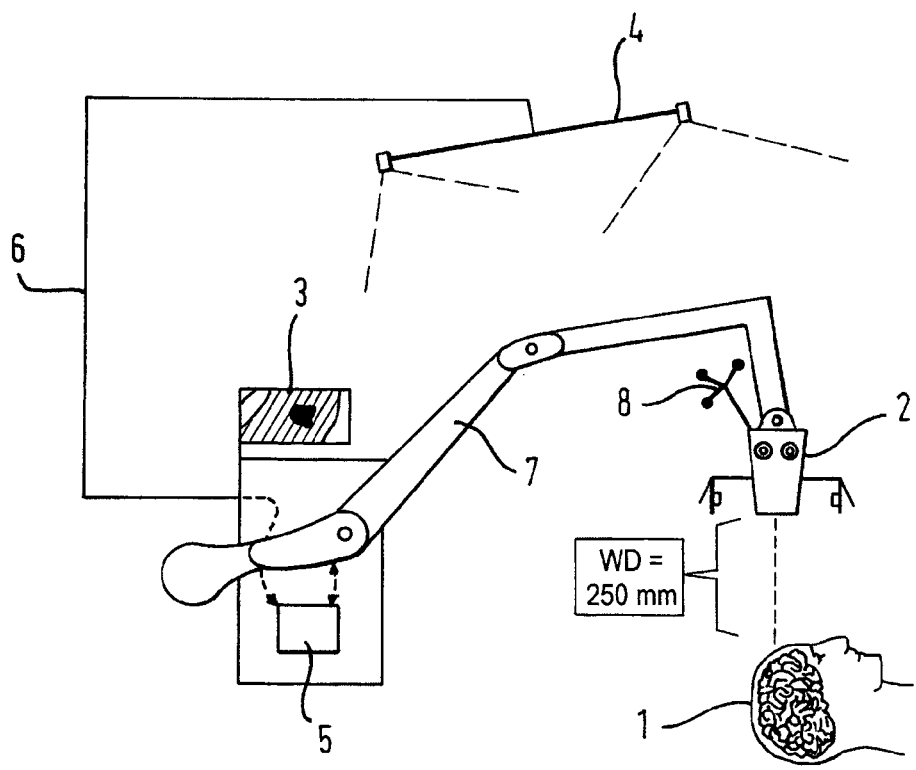
FIG. 1 shows a setup for determining and outputting the interval indication data if the optical parameter lies in the predetermined interval.
Figure 1:
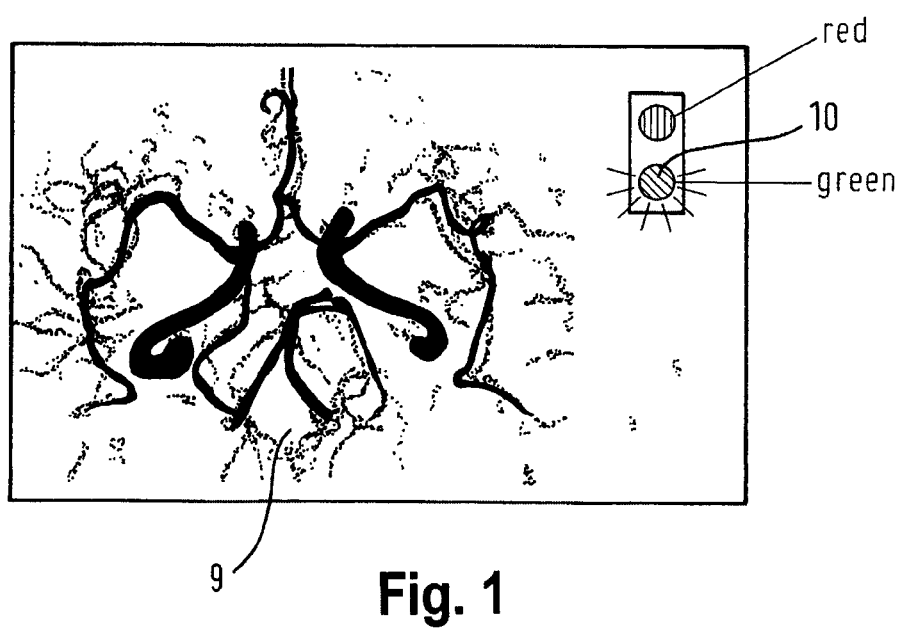

The predetermined interval for the working distance defined by the optical parameter interval data is generally a working distance of <300 mm. In the case of FIG. 1, the working distance therefore lies in the predetermined interval and the user is supplied with corresponding visual information (embodying the interval indication data) indicating to him that the optical parameter is lying in the predetermined interval. The visual information is embodied by a flashing or constantly activated green light 10 rendered in the display of the monitor 3. Furthermore, the subset 9 of the anatomical structure representation data is selected to contain only parts of a brain vessel structure fulfilling a predetermined size criterion at a working distance of 250 mm.

Common diameters of intra-cranial arteries which shall be displayed as an overlay on the image of the anatomical body part acquired by the digital microscope 2 at a working distance of 250 mm and full magnification are:

Carotis interna: about 3 mm
Ophthalmica: 1.0 to 1.5 mm
Choroidea anterior: about 0.5 mm
Cerebri media: 2.7 mm, Cerebri anterior: 2.1 mm, Cerebri posterior: 2.1 mm
Communicans anterior: 2.0 to 2.5 mm, Communicans posterior: 1.2 mm
Basilaris: about 3 mm These parts of the brain vessel tree are therefore displayed as an overlay on the image captured by the digital microscope 2 and rendered by the display of the digital microscope 2. The overlay is defined by the subset 9 of the anatomical structure representation data in the setup of FIG. 1.

Figure 2:
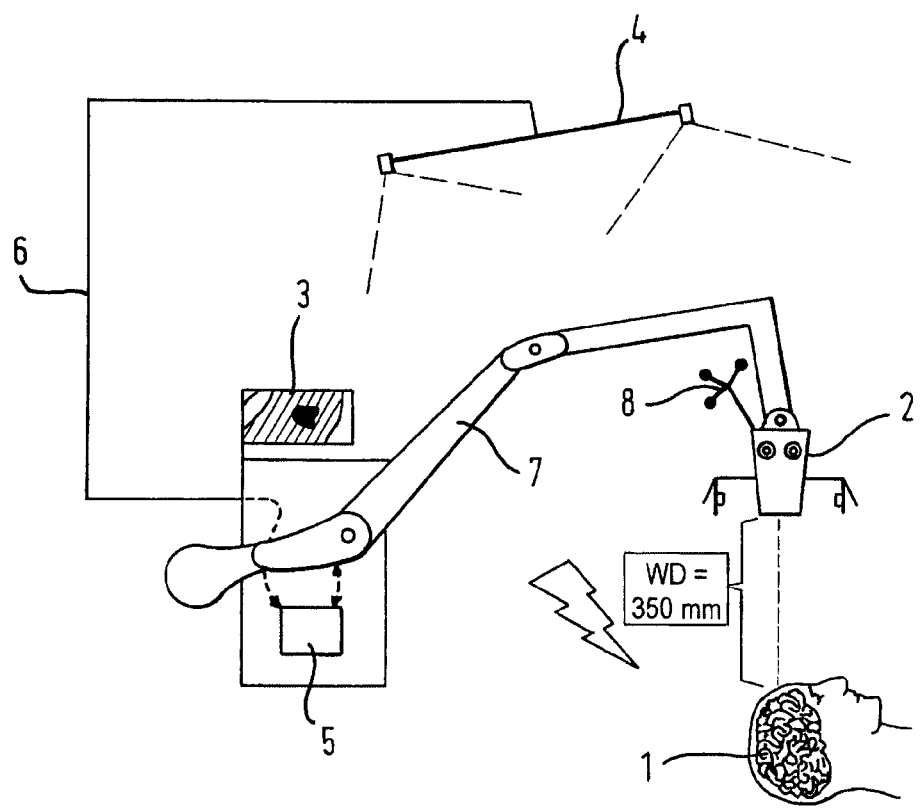
FIG. 2 shows a setup for determining and outputting the interval indication data if the optical parameter does not lie in the predetermined interval.
Figure 2:
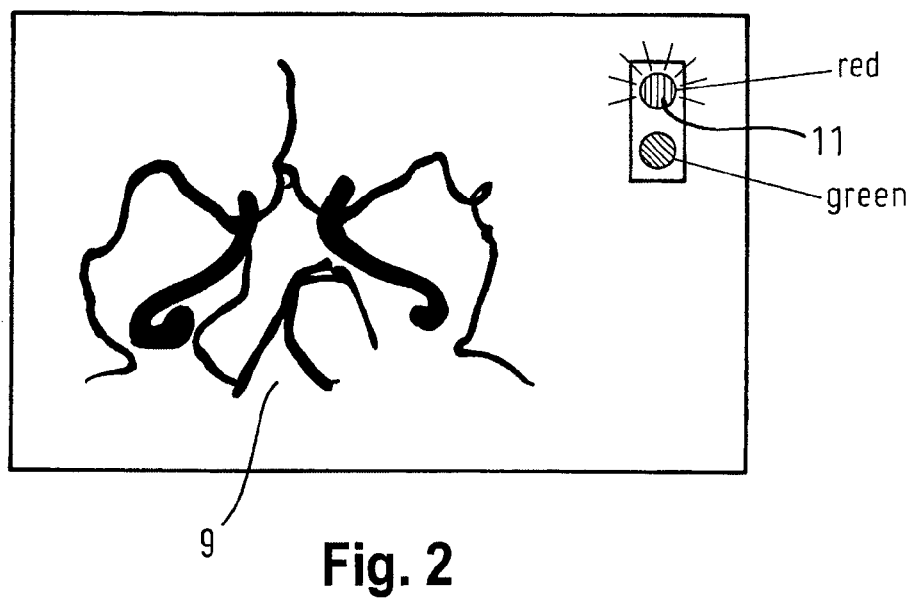

FIG. 2 shows essentially the same setup as FIG. 1 with the difference that the chosen working distance is 350 mm. Since this working distance does not lie in the predetermined interval of WD<300 mm, the user is presented with a flashing or constant red light 11 as visual information (embodying the interval indication data) that the working distance is not in the predetermined interval and that using the setup at this working distance does not allow to include the following vessels in the structure subset of the vessel tree, since at a working distance of more than 300 mm, vessels having a diameter less than 2 mm will not be shown in the image overlay anymore:

Ophthalmica: 1.0 to 1.5 mm
Choroidea anterior: about 0.5 mm
Communicans posterior: about 1.2 mm

The invention claimed is:

1. A medical imaging device, comprising:
an optical imaging apparatus;
a display apparatus operably coupled to the optical image apparatus;
at least one computer that is operably coupled to the optical imaging apparatus and the display apparatus and which comprises at least one processor, the computer being operably coupled to a non-transitory computer-readable data storage medium storing a program which, when executed by the at least one processor, causes the at least one computer to execute medical data processing method of determining anatomical structure subset data describing a subset of a graphical representation of an anatomical structure of a patient's body to be displayed simultaneously with a medical image of an anatomical body part, the method comprising executing, by at least one processor of the at least one computer, steps of:
acquiring, at the at least one processor, predetermined anatomical structure representation data describing a graphical representation of the anatomical structure and its position in the patient's body;
acquiring, at the at least one processor, anatomical body part image data describing an image of an anatomical body part of the patient imaged by an optical imaging apparatus for display by a display apparatus;
acquiring, at the at least one processor, optical parameter data describing a value of an optical parameter serving as a basis for displaying the anatomical body part image data;
acquiring optical parameter interval data describing a predetermined interval of values for the optical parameter in which the anatomical structure subset data can be determined;
determining, based on the optical parameter data and the optical parameter interval data, whether the value of the optical parameter lies within the interval of values for the optical parameter;
determining, by the at least one processor and on condition that the value of the optical parameter lies within the interval of values for the optical parameter and based on the anatomical structure representation data and the anatomical body part image data and the optical parameter data, anatomical structure subset data describing a real subset of the anatomical structure representation data, which real subset describes a graphical representation of a structure subset of the anatomical structure to be displayed simultaneously with the image of the anatomical body part, the real subset of the anatomical structure representation data comprising less information than the total image information contained in the anatomical structure representation data,
the anatomical structure subset data being determined based on a size of parts of the anatomical structure contained in the structure subset; and
determining, by the at least one processor on condition that the value of the optical parameter lies within the interval of values for the optical parameter, interval indication data describing information to be output to an associated user indicating that the optical parameter lies in the predetermined interval of values for the optical parameter.

2. A medical data processing method of determining anatomical structure subset data describing a subset of a graphical representation of an anatomical structure of a patient's body to be displayed simultaneously with a medical image of an anatomical body part, the method comprising executing, by at least one processor of at least one computer, steps of:
acquiring, at the at least one processor, predetermined anatomical structure representation data describing a graphical representation of the anatomical structure and its position in the patient's body;
acquiring, at the at least one processor, anatomical body part image data describing an image of an anatomical body part of the patient imaged by an optical imaging apparatus for display by a display apparatus;
acquiring, at the at least one processor, optical parameter data describing a value of an optical parameter serving as a basis for displaying the anatomical body part image data;
acquiring optical parameter interval data describing a predetermined interval of values for the optical parameter in which the anatomical structure subset data can be determined;
determining, based on the optical parameter data and the optical parameter interval data, whether the value of the optical parameter lies within the interval of values for the optical parameter;
determining, by the at least one processor and on condition that the value of the optical parameter lies within the interval of values for the optical parameter and based on the anatomical structure representation data and the anatomical body part image data and the optical parameter data, anatomical structure subset data describing a real subset of the anatomical structure representation data, which real subset describes a graphical representation of a structure subset of the anatomical structure to be displayed simultaneously with the image of the anatomical body part, the real subset of the anatomical structure representation data comprising less information than the total image information contained in the anatomical structure representation data, the anatomical structure subset data being determined based on a size of parts of the anatomical structure contained in the structure subset; and determining, by the at least one processor on condition that the value of the optical parameter lies within the interval of values for the optical parameter, interval indication data describing information to be output to an associated user indicating that the optical parameter lies in the predetermined interval of values for the optical parameter.

3. The method according to claim 2, wherein the optical parameter is a specific focus position that is at least one of a real focal length and a working distance at which the image of the anatomical body part is imaged by the optical imaging apparatus.

4. The method according to claim 2, wherein the optical parameter is a specific focus position that is a virtual focal length, at which the image of the anatomical body part is or is to be displayed by the display apparatus.

5. The method according to claim 2, further comprising:
determining, by the at least one processor and based on the anatomical structure subset data and the anatomical body part image data, display data describing a combined image comprising the image of the anatomical body part and an image generated from the subset of the anatomical structure representation data.

6. The method according to claim 5, wherein the combined image includes an overlay of the graphical representation of the subset of the anatomical structure on the image of the anatomical body part.

7. The method according to claim 5 comprising a step of displaying the combined image on the display apparatus.

8. The method according to claim 2, wherein the optical imaging apparatus includes a lens having a variable focus that is a focus lens including a zoom mechanism, and is a digital microscope or a digital camera.

9. The method according to claim 2, wherein the information to be output to a user is visual information that is characterised by a specific colour.

10. The method according to claim 2, further comprising:
determining, by the at least one processor and based on the optical parameter interval data and the optical parameter data, optical parameter variation data describing a direction in which the optical parameter has to be varied to allow determination of the anatomical structure subset data, wherein the interval indication data comprises the optical parameter variation data.

11. The method according to claim 2, wherein
the anatomical structure image data comprises class information describing classes which define structure subsets of the anatomical structure, wherein
each structure subset denotes a part of the anatomical structure which has a predetermined size and is associated with a predetermined value of the optical parameter, and wherein
the anatomical structure subset data is determined, by the at least one processor, based on determining the structure subset which is associated with the actual value of the optical parameter.

12. The method according to claim 11, wherein the size of the part of the anatomical structure contained in a respective one of the classes becomes smaller the smaller or larger the associated value of the optical parameter becomes.

13. A non-transitory computer-readable data storage medium storing a program which, when executed by at least one processor of at least one computer, causes the at least one computer to execute a medical data processing method of determining anatomical structure subset data describing a subset of a graphical representation of an anatomical structure of a patient's body to be displayed simultaneously with a medical image of an anatomical body part, the method comprising executing, by the at least one processor of at least one computer, steps of:

acquiring, at the at least one processor, predetermined anatomical structure representation data describing a graphical representation of the anatomical structure and its position in the patient's body;

acquiring, at the at least one processor, anatomical body part image data describing an image of an anatomical body part of the patient imaged by an optical imaging apparatus for display by a display apparatus;

acquiring, at the at least one processor, optical parameter data describing a value of an optical parameter serving as a basis for displaying the anatomical body part image data;

acquiring optical parameter interval data describing a predetermined interval of values for the optical parameter in which the anatomical structure subset data can be determined;

determining, based on the optical parameter data and the optical parameter interval data, whether the value of the optical parameter lies within the interval of values for the optical parameter;

determining, by the at least one processor and on condition that the value of the optical parameter lies within the interval of values for the optical parameter and based on the anatomical structure representation data and the anatomical body part image data and the optical parameter data, anatomical structure subset data describing a real subset of the anatomical structure representation data, which real subset describes a graphical representation of a structure subset of the anatomical structure to be displayed simultaneously with the image of the anatomical body part, the real subset of the anatomical structure representation data comprising less information than the total image information contained in the anatomical structure representation data, the anatomical structure subset data being determined based on a size of parts of the anatomical structure contained in the structure subset; and determining, by the at least one processor on condition that the value of the optical parameter lies within the interval of values for the optical parameter, interval indication data describing information to be output to an associated user indicating that the optical parameter lies in the predetermined interval of values for the optical parameter.

14. A computer operably coupled to the non-transitory computer-readable data storage medium according to claim 13.

* * * * *